US012622711B2

(12) United States Patent
Pressacco et al.

(10) Patent No.: US 12,622,711 B2
(45) Date of Patent: May 12, 2026

(54) POSITIONING DEVICE FOR IMPLANTATION OF PROSTHESIS IN A LONG BONE, IN PARTICULAR FOR IMPLANTATION OF HUMERAL PROSTHESIS

(71) Applicant: Limacorporate S.p.A., San Daniele del Friuli (IT)

(72) Inventors: Michele Pressacco, Martignacco (IT); Andrea Fattori, Cividale del Friuli (IT); Antony Pranzetti, Sommacampagna (IT)

(73) Assignee: Limacorporate S.p.A., San Daniele del Friuli (IT)

( * ) Notice: Subject to any disclaimer, the term of this patent is extended or adjusted under 35 U.S.C. 154(b) by 108 days.

(21) Appl. No.: 18/579,359

(22) PCT Filed: Jul. 6, 2022

(86) PCT No.: PCT/EP2022/068764
§ 371 (c)(1),
(2) Date: Jan. 14, 2024

(87) PCT Pub. No.: WO2023/285244
PCT Pub. Date: Jan. 19, 2023

(65) Prior Publication Data
US 2024/0335205 A1     Oct. 10, 2024

(30) Foreign Application Priority Data
Jul. 15, 2021     (IT) ........................ 102021000018728

(51) Int. Cl.
*A61B 17/17*        (2006.01)
*A61F 2/46*         (2006.01)

(52) U.S. Cl.
CPC ........ *A61B 17/1778* (2016.11); *A61F 2/4612* (2013.01); *A61F 2002/4628* (2013.01)

(58) Field of Classification Search
CPC .................. A61F 2/4607; A61F 2/4612; A61F 2002/4628; A61F 2002/4625; A61B 17/1717; A61B 17/1778; A61B 17/164
See application file for complete search history.

(56) References Cited

U.S. PATENT DOCUMENTS 6,277,123 B1 * 8/2001 Maroney ............... A61F 2/4657
                                                    606/99
8,123,753 B2 * 2/2012 Poncet .................. A61F 2/4637
                                                    606/87

(Continued)

FOREIGN PATENT DOCUMENTS

WO        2020/072466 A1     4/2020

OTHER PUBLICATIONS

International Search Report dated Sep. 26, 2022 issued in connection with PCT/EP2022/068764.

(Continued)

*Primary Examiner* — Anu Ramana
(74) *Attorney, Agent, or Firm* — Nixon Peabody LLP

(57)        ABSTRACT

The present invention relates to a positioning device (100) for implantation of prosthesis in a long bone, in particular for implantation of humeral prosthesis, comprising: at least one centering element (101) with a channel (102) configured to house an intramedullary nail (11); a support element (103) configured to hold a reference mask (200) on a plane (12) at a resected metaphysis of the long bone; an adjustment element (104) configured to connect the centering element (101) and the support element (103), wherein the adjustment element (104) further comprises a displacement device (105) configured to provide a controlled offset to the support (Continued)

element (103) for displacing the reference mask (200) over the plane (12) of the resected metaphysis.

16 Claims, 5 Drawing Sheets

(56)                    References Cited

U.S. PATENT DOCUMENTS

| | | | |
|---|---|---|---|
| 8,197,487 B2 | 6/2012 | Poncet et al. | |
| 8,241,289 B2 * | 8/2012 | Maisonneuve .... | A61B 17/1778 |
| | | | 606/80 |
| 8,246,621 B2 * | 8/2012 | Poncet ............... | A61B 17/1778 |
| | | | 606/82 |
| 8,480,677 B2 * | 7/2013 | Groh ..................... | A61F 2/4612 |
| | | | 606/86 R |
| 8,979,847 B2 * | 3/2015 | Belcher .............. | A61B 17/1675 |
| | | | 606/79 |
| 10,709,460 B2 * | 7/2020 | Nelson ................... | A61B 17/17 |
| 10,888,438 B2 | 1/2021 | Groh | |
| 2016/0030196 A1 * | 2/2016 | Eraly ................... | A61F 2/4612 |
| | | | 606/96 |

OTHER PUBLICATIONS

Written Opinion dated Sep. 26, 2022 issued in connection with PCT/EP2022/068764.
International Preliminary Report on Patentability dated Jun. 5, 2023 issued in connection with PCT/EP2022/068764.

* cited by examiner

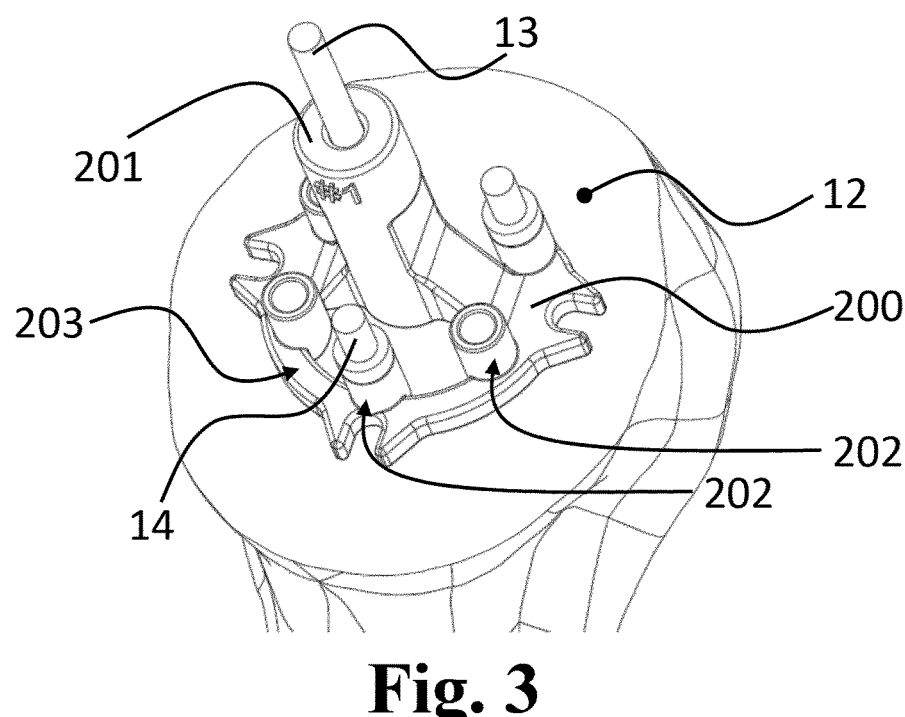
Fig. 3
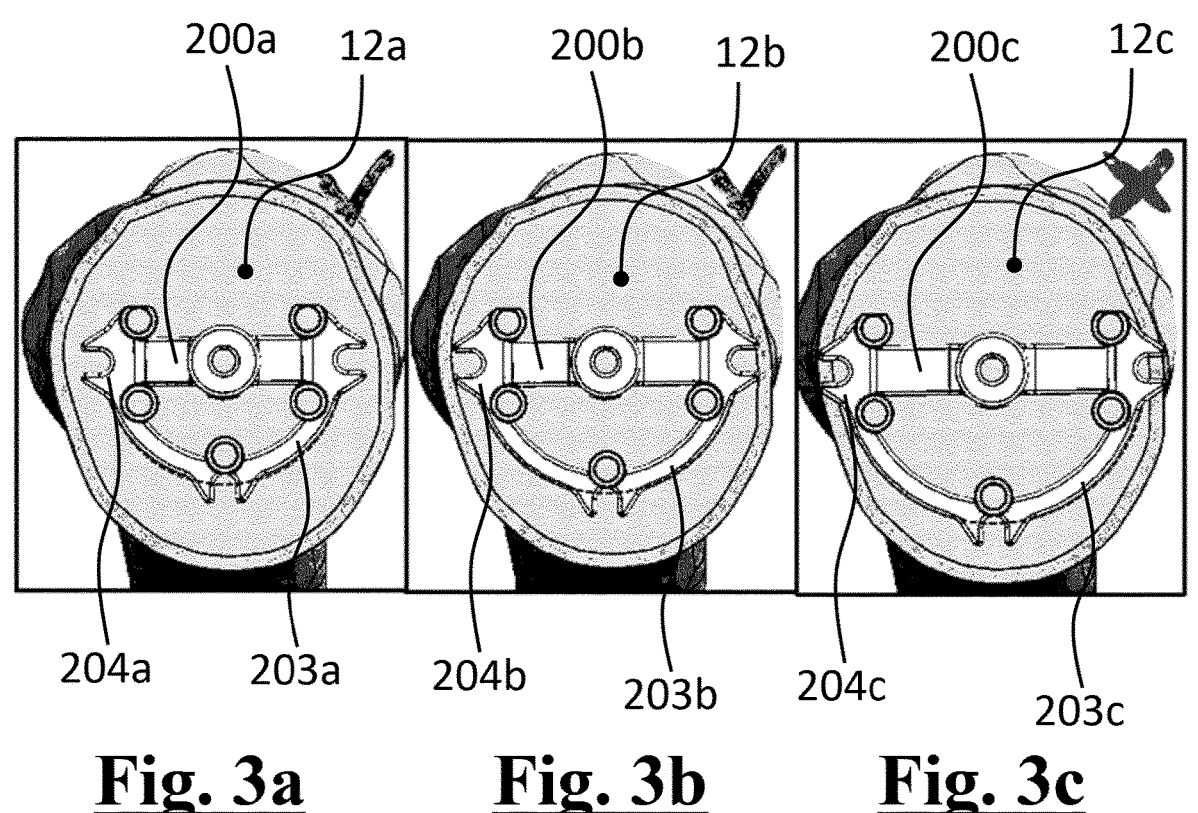
Fig. 3a          Fig. 3b          Fig. 3c

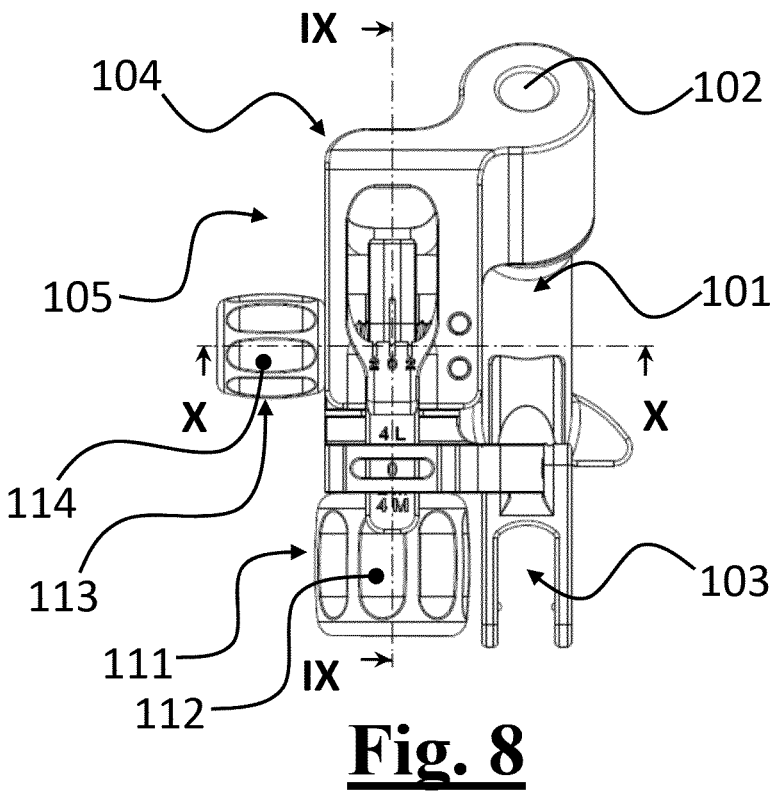
Fig. 8
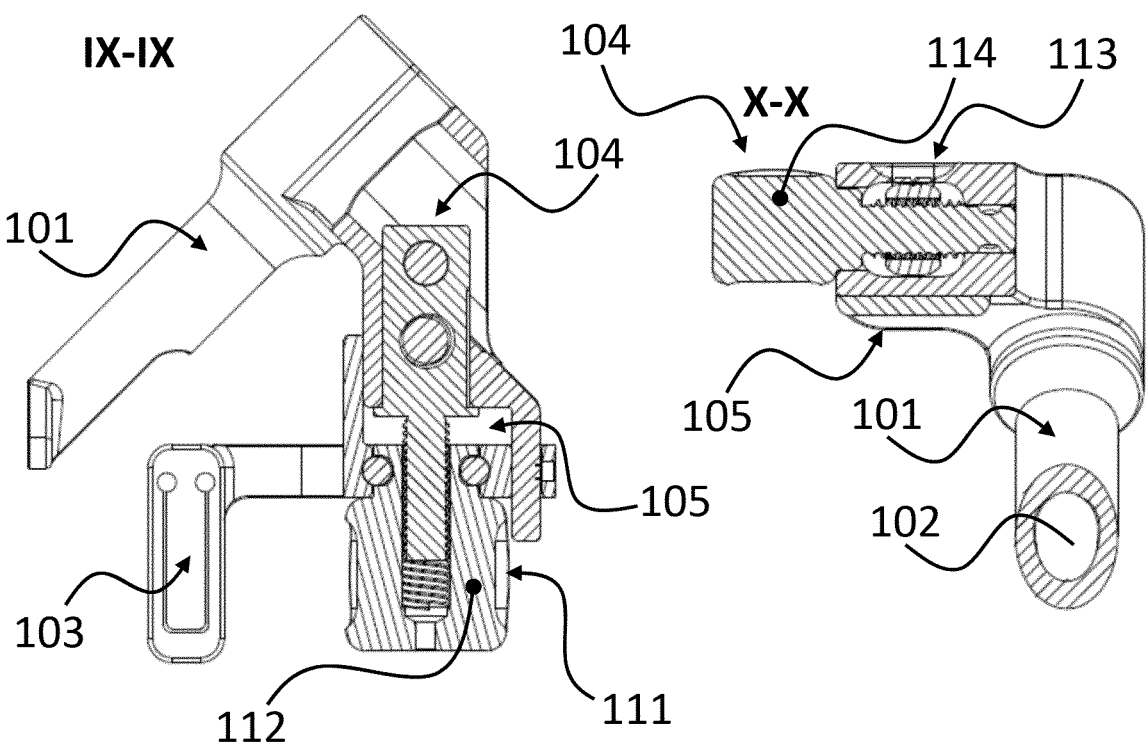
Fig. 9                    Fig. 10

POSITIONING DEVICE FOR IMPLANTATION OF PROSTHESIS IN A LONG BONE, IN PARTICULAR FOR IMPLANTATION OF HUMERAL PROSTHESIS

CROSS-REFERENCE TO RELATED APPLICATIONS

This application is a national phase of PCT/EP2022/068764, filed Jul. 6, 2022, and claims priority to Italian Patent Application No. 102021000018728, filed Jul. 15, 2021, the entire contents of both of which are hereby incorporated by reference.

FIELD OF APPLICATION

The present invention relates to a positioning device for implantation of prosthesis in a long bone, in particular for implantation of humeral prosthesis.

The invention is particularly useful in shoulder prosthesis implantation surgery, in particular of modular shoulder prosthesis both of the anatomical and inverse type; the following description is made with reference to this specific field of application to simplify the exposure thereof.

In general, the invention may be used to find an appropriate positioning at a metaphyseal surface of a long bone and to fasten a reference thereat, such as a Kirschner wire, which can be used for further operations during a prosthesis implantation.

PRIOR ART

In the shoulder prosthesis field, the use of prostheses, typically modular prostheses consisting of a plurality of elements that may be combined together to obtain an anatomical or inverse prosthesis, is now widespread.

In the surgical implantation of a prosthesis, it is not always immediate to find a positioning that allows having the prosthesis device well centered in the metaphysis, as well as a prosthesis stem well centered in the bone canal.

In fact, in the example of a shoulder prosthesis there are a first Medio-Lateral (M-L) offset, and a second Antero-Posterior (A-P) offset between the prosthesis stem and the humeral head.

The most common modular prostheses are made with a symmetrical stem, and not with different stems for right shoulder and left shoulder, therefore a structural correction of the A-P offset is not provided for in the modular prosthesis.

Instead, the most common modular prostheses are made with a predetermined correction of M-L offset, which however is selected according to a design corresponding to a literature average value; this predetermined correction is therefore not necessarily the most suitable one for each individual patient in the entire humeral population.

In addition, many types of current modular prostheses, especially those with long stems, base the positioning of the stem by referring to the axis of the bone shaft as they are precisely designed for a distal fixation and grip in the shaft itself; to then allow a correct positioning of the prosthetic component of the humeral head (also modular) that is connected to the stem, the latter is generally supplied with different eccentric offsets in order to compensate for the pre-existing anatomical offsets and thus to ensure an optimal positioning.

In order to develop ever less invasive and conservative prosthetic components, recently new designs of short stem prostheses are being developed, whose fixation tends to be less and less distal and more proximal (in the metaphyseal area of the bone).

However, as a consequence of these new designs of short stem prostheses, if the prosthesis centering occurred based on the metaphysis morphology, it could happen that the stem of the prosthesis collides with the walls of the diaphyseal bone cortex, leading to a non-optimal positioning of the prosthesis implantation. Vice versa, if the prosthesis centering occurred with respect to the bone canal, it could happen that the prosthesis component comes into conflict with the metaphyseal cortices, with the risk of localized bone fracture; furthermore, having these short stem prostheses a much more proximal fixation, inadequate metaphyseal positioning could lead to inadequate fixation.

An object of the present invention is to allow the correct positioning of a reference, such as for example a Kirschner wire, which acts as a guide for an implantation of a metaphyseal component of a prosthesis, be it anatomical or inverse, in a long bone.

A further object of the present invention is also to allow the correct positioning of a reference on a metaphyseal surface, for a better positioning of a prosthesis component, in particular of a humeral shoulder prosthesis, be it preferably with a short stem or even with a long stem.

A further object of the present invention is to provide a positioning device having structural and functional features such as to overcome the drawbacks of the prior art.

SUMMARY OF THE INVENTION

The solution idea underlying the present invention is to make a mechanical guide that allows a centering in the bone canal and, knowing the diameter thereof specific for the patient starting from radiographs or CT scans, obtaining an indication of how much offset may be applied to the prosthesis stem in order to optimally position the prosthesis on the metaphysis.

The positioning tool supplied with the prosthesis, starting from the canal reference, allows determining an initial position of the prosthesis and, if it is not centered on the metaphysis, it allows applying an offset, in particular a first A-P offset and a second M-L offset, for displacing the position of the prosthesis into a correct metaphyseal position.

Based on this solution idea, a positioning device for implantation of prosthesis in a long bone, in particular for implantation of humeral prostheses, is provided, comprising: at least one centering element with a channel configured to house un intramedullary nail; a support element configured to hold a reference mask on a plane at a resected metaphysis of the long bone; an adjustment element configured to connect the centering element and the support element, wherein the adjustment element further comprises a displacement device, configured to provide a controlled offset to the support element for displacing the reference mask over the plane of the resected metaphysis.

In this way, the positioning device of the present invention allows positioning the reference mask in the most proper position on the metaphysis for the subsequent implantation of the prosthesis. In particular, the adjustment element allows providing a controlled offset to the support element that holds the reference mask, to suitably control a position with respect to the intramedullary nail.

Advantageously, the present invention allows a prosthesis to be positioned in such a way as to avoid conflicts within the bone canal.

Advantageously, the present invention allows a more accurate and repeatable positioning of a metaphyseal reference, consisting for instance of a Kirschner wire, used during the implantation of the prosthesis, in particular of a humeral shoulder prosthesis.

Preferably, the positioning device provides for movement slides in directions perpendicular to each other, for instance a medio-lateral direction of prosthesis and an antero-posterior direction of prosthesis, so that a displacement device adjustment system may provide a controlled offset over the resected metaphyseal plane.

Preferably, the reference mask is removably associated with the support element and is configured to implant an appropriate reference, such as a Kirschner wire, useful for subsequent operations of the prosthesis implantation, on the metaphyseal resected surface.

Preferably, the adjustment element is laterally offset with respect to the centering element and to the support element, so as to advantageously allow the surgeon an unobstructed upper access to the reference mask, and so as to simplify the installation of the metaphyseal reference.

Further features and advantages of the invention will become clearer from the following detailed description of embodiments, given by way of non-limiting example, and from the claims which are an integral part of the present description.

BRIEF DESCRIPTION OF THE DRAWINGS

FIG. 3 shows a reference mask according to the present invention applied at a humeral metaphysis;

FIGS. 3*a*, 3*b*, 3*c* show different reference mask sizes according to the present invention applied at different humeral metaphysis;

FIG. 8 shows the adjustment element of the positioning device of FIG. 1;

FIG. 9 shows a first sectional view of FIG. 8;

FIG. 10 shows a second sectional view of FIG. 8.

In different figures, similar elements will be indicated by similar reference numbers.

DETAILED DESCRIPTION

Figure 1:
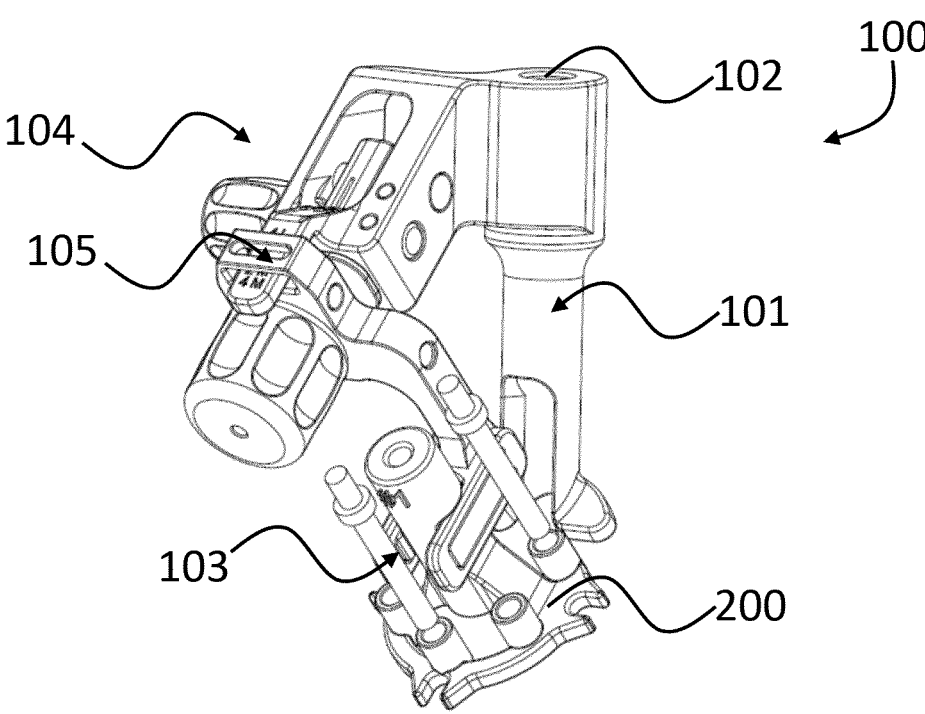
FIG. 1 shows a perspective view of an embodiment of a positioning device according to the present invention.

FIG. 1 shows a perspective view of an embodiment of a positioning device 100 according to the present invention.

The positioning device 100 is intended as an aid for prosthesis implantation in a long bone. In particular, said positioning device 100 is particularly configured for implantation of a humeral modular prosthesis, and the following description will refer to this example.

The positioning device comprises at least one centering element 101 with a channel 102 configured to house an intramedullary nail.

The positioning device further comprises a support element 103 configured to hold a reference mask 200 at a plane of a resected metaphysis of a long bone.

The positioning device further comprises an adjustment element 104 configured to connect the centering element 101 and the support element 103.

In particular, the adjustment element 104 is preferably, but not limitedly, configured to keep a spatial angle between the centering element 101 and the support element 103. In possible variants, the adjustment element could be configured to keep different spatial angles between the centering element 101 and the support element 103, for instance in a variable or adjustable manner, thus allowing to adapt to the implantation of different prostheses.

The adjustment element 104 further comprises a displacement device 105 configured to provide a controlled offset to the support element 103 for displacing the reference mask 200 in a controlled manner on a bone metaphysis.

Figure 2:
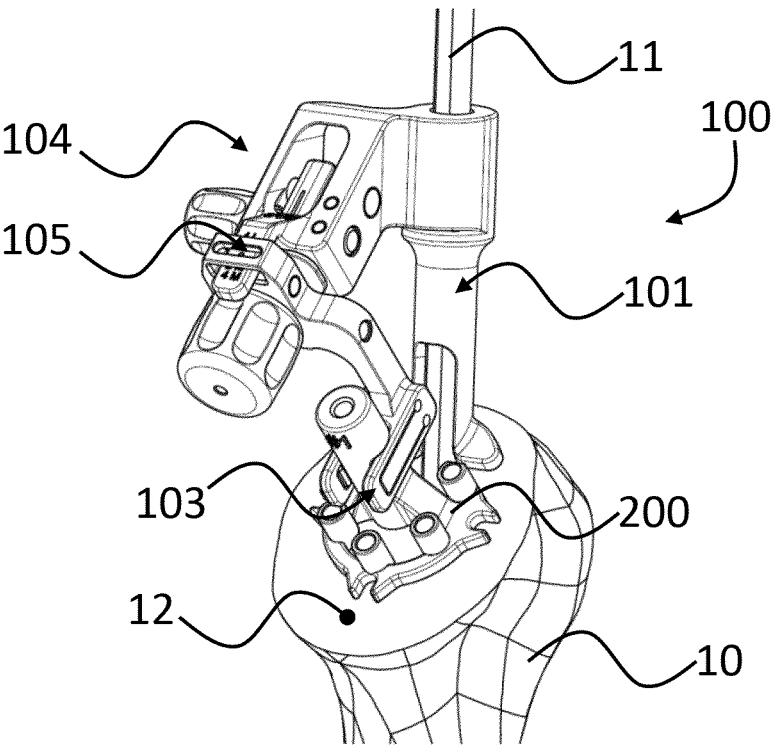
FIG. 2 shows the positioning device of FIG. 1 applied to a humeral end.

FIG. 2 shows the positioning device 100 applied to a humeral end 10.

As already described, the channel 102 of the centering element 101 is configured to house an intramedullary nail 11, inserted in the humeral end 10.

Moreover, the support element 103 is configured to hold the reference mask 200 on a plane 12 at the resected metaphysis of the humeral end 10. In this specific example, the positioning device 100 is positioned on the resected metaphysis plane 12 of a humerus 10, through the channel 102 being made to slip onto the intramedullary nail 11 used as diaphyseal reference of the system.

As it will be described hereinafter in greater detail, the displacement device 105 is configured to provide a controlled offset to the support element 103, so as to displace the reference mask 200 on the metaphysis plane 12 in a controlled manner.

FIG. 3 shows the reference mask 200 applied at the humeral metaphysis plane 12. The reference mask 200 is preferably an accessory component of the positioning device 100.

The reference mask 200 is removably associated with the support element 103, for instance by means of a clip system. In particular, the reference mask 200 comprises a main seat 201 configured to implant a metaphyseal reference 13 on the metaphysis plane 12.

Types of metaphyseal references usable in cooperation with the positioning device 100 of the present invention not limitedly include: K-wires or Steinmann pins or other types of pins.

Preferably, the reference mask 200 further comprises a plurality of auxiliary seats 202 (just some of which are identified in the figure) configured to house temporary fastening pins 14, to hold the reference mask 200 in position on the plane 12 of the resected metaphysis once separated from the support element 103. In fact, it may happen that, for several reasons, it is not possible to insert the metaphyseal reference when the positioning device is applied, due to its overall dimensions; in this case, it is possible to fasten the reference mask 200 through the temporary fastening pins 14, to remove the assembly of the positioning device 100 and afterwards to proceed fastening the metaphyseal reference 13.

Preferably, the reference mask 200 comprises a semicircular reference 203, which matches an outer dimension of a circular housing of an associated modular prosthesis component, and whose operation will be further described.

Preferably, the reference mask 200 is provided in modular sizes, corresponding to sizes of modular components of prosthesis, to better adapt to the specific anatomy of the patient.

FIGS. 3a, 3b, 3c illustrate different reference mask sizes according to the present invention, applied at different humeral metaphysis.

The reference mask 200a is correctly positioned substantially in the middle of the metaphysis 12a; moreover, the reference mask 200a corresponds to a suitable size of prosthesis component since the semi-circular reference 203a does not risk interfering with the metaphyseal cortex.

The reference mask 200b is correctly positioned substantially in the middle of the metaphysis 12b; moreover, the reference mask 200b corresponds to a size of prosthesis component which is of limit size, since the semi-circular reference 203b is at the limit so as not to interfere with the metaphyseal cortex.

Finally, even if the reference mask 200c is correctly positioned substantially in the middle of the metaphysis 12c, the reference mask 200c corresponds to a size of prosthesis component which is excessive in dimension and the semi-circular reference 203c actually risks to interfere with the metaphyseal cortex.

To assist the surgeon in selecting the appropriate prosthesis component size, the reference mask 200 comprises a plurality of references, in particular three references (in the respective images, only one is indicated as 204a, 204b, 204c, respectively) configured externally to the semi-circular reference and indicative of a minimum distance to be kept with respect to a metaphyseal cortex.

Preferably, said references have an extension of about 3 mm beyond the semi-circular reference, allowing to determine an optimal position on the metaphysis plane 12 for the mask 200 and thus for the prosthesis component, which ensures a minimum distance from the metaphyseal cortex, thus avoiding the risk for the prosthesis component to fracture the cortex.

Figure 4:
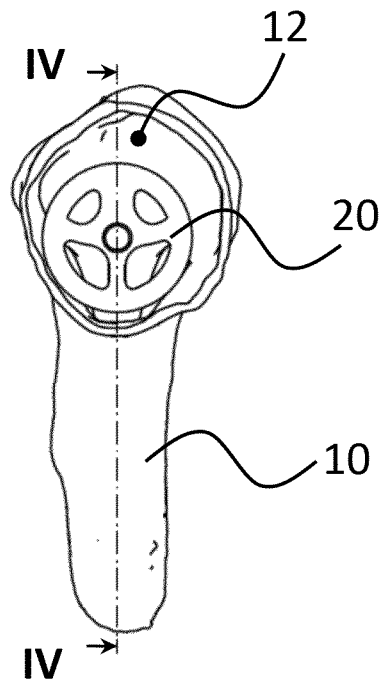
FIG. 4 exemplifies a humeral prosthesis component applied in a non-optimal position with respect to a metaphyseal cortex.
Figure 5:
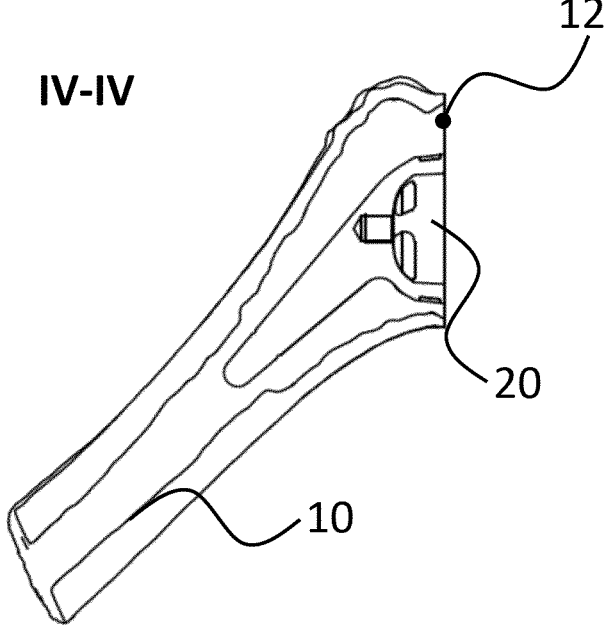
FIG. 5 represents a sectional view of FIG. 4.

FIG. 4 and FIG. 5 exemplify a humeral prosthesis component 20 applied in a non-optimal position with respect to a metaphyseal cortex of a humerus 10.

In this example, it is shown that even a "perfect" diaphyseal placement (visible in FIG. 5, wherein the stem of the prosthesis component 20 is perfectly aligned to the channel, therefore without M-L offset and without A-P offset) however corresponds, for the exemplified anatomy, to a "non-perfect" metaphyseal positioning of the prosthesis component 20 (visible in FIG. 4, with respect to the cortex).

Precisely to correct the metaphyseal positioning of the prosthesis component 20 according to a compromise with the diaphyseal positioning, the positioning device 100 provides the displacement device 105 which is configured for displacing, in directions perpendicular to each other over a plane of the metaphysis plane 12, the reference mask 200 that corresponds to the final positioning of the prosthesis component 20. Said displacement device 105 and its operation will be herein further described.

Figure 6:
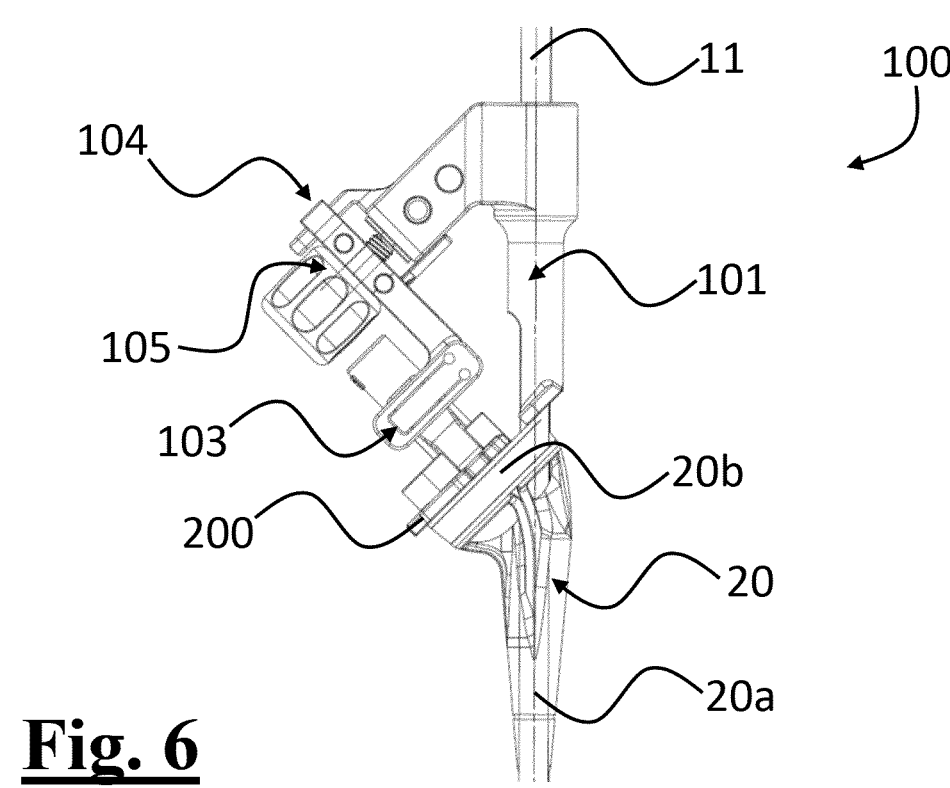
FIG. 6 shows a first plan view of the positioning device of FIG. 1.

FIG. 6 shows a view from the side of the positioning device 100.

As visible in the figure, the adjustment element 104 mechanically connects the centering element 101 and the support element 103, preferably making an interposed L-shaped structure. A first end of the adjustment element 104 defines a spatial angle with respect to the axis of the centering element 101, whereas a second end of the adjustment element 104 is connected to the support element 103, so as to allow displacing the reference mask 200 over a resection plane 12 of the metaphysis in a tangential manner. Preferably, the resection plane 12 is inclined of the same spatial angle with respect to the axis of the centering element 104. Preferably, the second end of the adjustment element 104 is in particular perpendicular to a plane which the reference mask 200 belongs to.

Preferably, the spatial angle between the centering element 101 and the support element 103 corresponds to a spatial angle between a stem 20a of the prosthesis component 20 and an upper housing 20b of the prosthesis component 20. In other embodiments, the modular prosthesis may not be of the short stem type, but for instance it provides a long stem and an upper housing separatable from each other.

Figure 7:
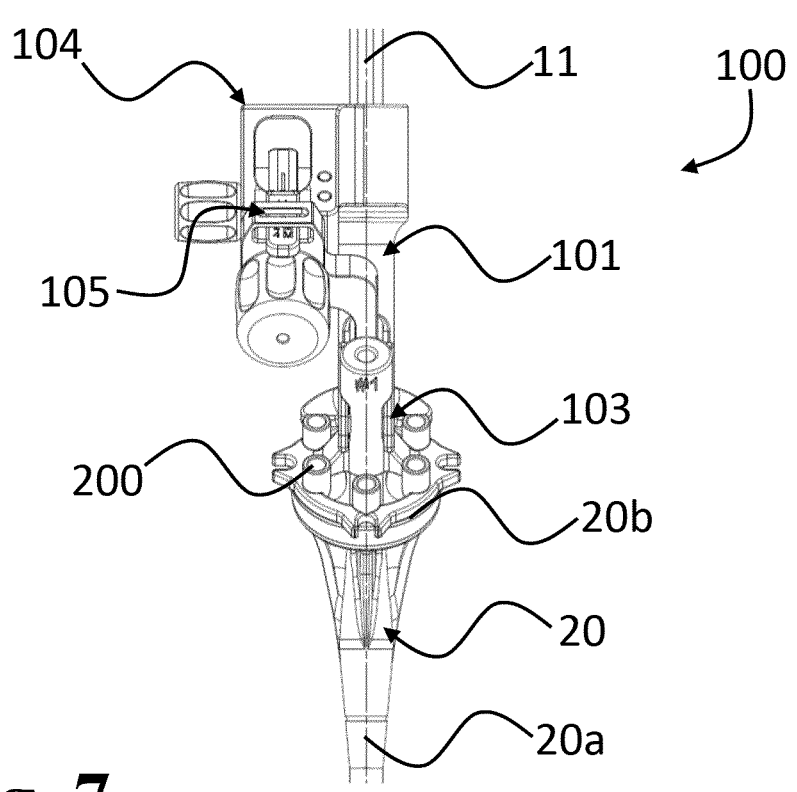
FIG. 7 shows a second plan view of the positioning device of FIG. 1.

FIG. 7 shows a front view of the positioning device 100.

As visible in the figure, the adjustment element 104 is laterally offset with respect to the centering element 101 (in the example of the image, offset to the left) and to the support element 103, to allow an unobstructed upper access for the surgeon (in the example of the image, preferably with the right hand) to the reference mask 200. In this way, it becomes easier, where possible, to insert the metaphyseal reference 13 into the reference mask 200, directly with the positioning device 100 assembled on site.

FIG. 8 shows the exemplifying embodiment of the adjustment element 104 in detail.

Preferably, the displacement device 105 of the adjustment element 104, comprises a first slide 111 translating in a medio-lateral direction of prosthesis and having a first adjustment system 112, and a second slide 113 translating in a anteroposterior direction of prosthesis and having a second adjustment system 114.

In the preferred embodiment, both the first adjustment system 112 and the second adjustment system 114 comprise predetermined position markings, which allow providing the offset in a controlled manner, by displacing the reference mask 200 at predetermined increases, both with a positive displacement and with a negative displacement with respect to an axis of the centering element 101.

As already described, the reference mask 200 is fixed to the positioning device 100, the purpose of said reference mask 200 being that of identifying the position of the final implantation at the plane 12 of the resected metaphysis; the position relating to the intramedullary nail 11 is instead identified by the markings present on the displacement device 105, associated with the first adjustment system 112 and with the second adjustment system 114.

In the preferred embodiment, the position identified as 0 ML (Medio-Lateral of prosthesis) and 0 AP (Antero-Posterior of prosthesis) in the markings is useful as a starting point for positioning the implantation. In this specific case, the 0 ML and 0 AP positions identify the position in which, proceeding with the surgical technique without inserting offsets, the prosthesis final implantation will be positioned aligned with the intramedullary nail 11.

In addition, the positioning device 100 allows for flexibility in the offset for positioning the metaphyseal reference 13 by adjusting the prosthesis Medio-Lateral position (ML) and the prosthesis Antero-Posterior position (AP) of the reference mask 200, in particular through the adjustment systems 112 and 114.

The adjustment systems 112 and 114 allow the surgeon to choose a compromise between metaphyseal and diaphyseal positions, in order to be able to implant the prosthesis without running the risk of bad positioning and/or humeral fracture.

FIG. 9 shows a first sectional view in which it is shown that the first slide 111 comprises a respective screw transmission, controlled by the first adjustment system 112.

Likewise, FIG. 10 shows a second sectional view in which it is shown that the second slide 113 comprises a respective screw transmission, controlled by the second adjustment system 114.

Thanks to the displacement device 105 of the present invention, it becomes possible to provide a controlled ML and AP offset to the support element 103, for displacing the reference mask 200 on the metaphysis. Therefore, advantageously, it becomes possible to accurately and repeatably position a reference 13 in the best position for a prosthesis implantation.

It is clear that the skilled person may make possible further implementations and changes of the present invention, to meet contingent needs.

For instance, the specific embodiment of the displacement device 105 may be modified by providing a different configuration of the slides and of the adjustment systems associated therewith.

The above-described embodiment is thus to be intended for illustrative and non-limiting purposes.

What is claimed is:

1. A positioning device for implantation of prosthesis in a long bone, the positioning device comprising:

at least one centering element including a channel configured to house an intramedullary nail;

a support element configured to hold a reference mask on a plane defined by a resected metaphysis of said long bone;

an adjustment element configured to connect said centering element and said support element, wherein said adjustment element further comprises a displacement device configured to provide a controlled offset to said support element, said displacement device including a first slide translating in a first direction parallel to said plane for displacing said reference mask in said first direction parallel to said plane, and said displacement device including a second slide translating in a second direction parallel to said plane for displacing said reference mask in the second direction parallel to said plane, the second direction being different to the first direction.

2. The positioning device according to claim 1, wherein said first slide includes a first adjustment system, and said second slide includes a second adjustment system.

3. The positioning device according to claim 2, wherein said first slide comprises a first threaded element controlled by the first adjustment system, and said second slide comprises a second threaded element controlled by the second adjustment system.

4. The positioning device according to claim 2, wherein said first adjustment system and said second adjustment system comprise predetermined position markings for providing said controlled offset by displacing said reference mask at predetermined increases, both with positive displacement and with negative displacement with respect to an axis of said centering element.

5. The positioning device according claim 1, wherein said adjustment element is laterally offset with respect to said centering element and to said support element to allow an unobstructed upper access to said reference mask.

6. The positioning device according to claim 1, further comprising a reference mask removably associated with said support element.

7. The positioning device according to claim 6, wherein said reference mask comprises a main seat configured to implant a metaphyseal reference on said resected metaphysis.

8. The positioning device of claim 7, wherein the metaphyseal reference comprises a Kirschner wire.

9. The positioning device according to claim 7, wherein said reference mask further comprises a plurality of auxiliary seats configured to house temporary fastening pins, for holding in position said reference mask once separated from said support element.

10. The positioning device according to claim 6, wherein said reference mask comprises a semi-circular portion matching an external dimension of an associated prosthesis component.

11. The positioning device according to claim 10, wherein said reference mask further comprises a plurality of references configured externally to said semi-circular reference and indicating a minimum distance of said reference mask with respect to a metaphyseal cortex of said long bone.

12. The positioning device according to claim 6, wherein the reference mask is provided in modular sizes corresponding to sizes of prosthesis modular components.

13. The positioning device according to claim 1, wherein said adjustment element mechanically connects said centering element and said support element providing a spatial angle with respect to an axis of said centering element so as to allow displacing said reference mask in a tangential manner over said plane, said plane being a resection plane of said metaphysis inclined at the spatial angle with respect to the axis of said centering element.

14. The positioning device according to claim 13, wherein said adjustment element provides a L-shaped structure, a first end of said adjustment element defining said spatial angle, a second end of said adjustment element being connected to said support element and being perpendicular to a plane of said reference mask.

15. The positioning device according to claim 1, wherein a spatial angle between said centering element and said support element corresponds to a spatial angle between a stem of an associated prosthesis component and an upper housing of the associated prosthesis component.

16. The positioning device according to claim 1, wherein the first direction and the second direction are perpendicular to each other.

* * * * *